(12) United States Patent
Darcey

(10) Patent No.: US 6,319,217 B1
(45) Date of Patent: Nov. 20, 2001

(54) CUSTOM-FITTING LUMBOSACRAL SUPPORT PAD

(75) Inventor: Thomas D. Darcey, Mooresville, NC (US)

(73) Assignee: BSN Medical, Inc., Wilmington, DE (US)

(*) Notice: Subject to any disclaimer, the term of this patent is extended or adjusted under 35 U.S.C. 154(b) by 0 days.

(21) Appl. No.: 09/265,918

(22) Filed: Mar. 10, 1999

(51) Int. Cl.[7] .................................................. A61F 5/00
(52) U.S. Cl. ................................................ 602/19; 128/845
(58) Field of Search ...................... 602/5, 8, 19; 128/845, 128/846, 882

(56) References Cited

U.S. PATENT DOCUMENTS 4,708,130 * 11/1987 Grudem ................................. 602/19
5,179,942 * 1/1993 Drulias .................................. 602/19
5,632,723 * 5/1997 Grim ....................................... 602/8
5,722,940 * 3/1998 Gaylord ................................. 602/19
5,842,475 * 12/1998 Duback ............................... 128/882
5,943,694 * 8/1999 Moureaux ................................ 2/2.5

* cited by examiner

Primary Examiner—Michael A. Brown
(74) Attorney, Agent, or Firm—Adams, Schwartz & Evans, P.A.

(57) ABSTRACT

A lumbosacral support pad for being custom-fitted to the lumbosacral area of the back and comprising an initially flexible fabric layer comprised of a fabric impregnated or coated with a moisture-curable resin which hardens upon curing to form a rigid structure which retains the shape into which it is molded during curing, a protective covering layer enclosing at least one major surface of the fabric layer, a moisture-proof protective pouch within which said lumbosacral support pad is sealed for storage in the absence of moisture until the pad is to be molded to the back.

7 Claims, 6 Drawing Sheets

CUSTOM-FITTING LUMBOSACRAL SUPPORT PAD

TECHNICAL FIELD AND BACKGROUND OF THE INVENTION

This invention relates to a custom-fitted lumbosacral support pad designed to fit within the pocket of a elastic lumbo-sacral support belt of the general type which encircles the body at level of the lumbosacral plexus. The support pad may be used to treat injury to the back or to prevent injury to the back, as in the case of supports commonly worn around the lower back by workers who are required to handle heavy loads.

Any great force can tear the muscles and tendons of the lower back in the region of the lumbosacral plexus. This type of injury is common in sports and work occupations that require pushing or pulling against great resistance, such as lifting a heavy weight from the ground or pushing against a heavy object. It also occurs in sports that require sudden twisting of the back; turning to dribble after a rebound in basketball, swinging a golf club in golf or swinging a bat in baseball.

Risk factors for lower back injury include an exaggerated curve of the lower spine, a pelvis that tilts forward, inflexible or weak back muscles, weak abdominal muscles and tight, inflexible hamstrings. The back is also prone to injury when the spine is weakened by arthritis, misaligned vertebrae, slipped or ruptured discs, or a spinal bone tumor.

A lower back injury usually causes sudden pain in the lower back during twisting, pushing, or pulling. Thereafter, the pain may momentarily subside, prompting further exercise and injury. As the torn muscle or tendon continues to bleed and swell, spasms occur, causing severe pain. Because the spasms can be aggravated by almost any movement, rest, compression, ice and support to the back are commonly prescribed treatments.

The invention takes advantage of polymer chemistry to permit quick and easy molding of a lumbosacral support pad to the lower back. Shock attenuation is increased since the custom fit spreads contact between the pad and the back over a wider surface area. The lumbosacral support pad according to the invention can be molded exactly to the shape of the back of the wearer, thus obtaining a more accurate and thus more protective fit. The lumbosacral support pad is then hold against the back by a lumbosacral support bolt having a pocket within which tho lumbosacral support pad fits, by an elastic bandage or other device.

Some prior art devices are pre-formed into a "universal" conformation designed to approximate the back conformation of the average user. In reality, such devices fit no one.

Other prior art devices include support pads which are constructed of thermosetting materials, which are heated and then formed to the body while heated. These products require a source of heat, and are susceptible to either over-or-underheating. In addition, body heat itself can soften or at least increase the flexibility of the pad, thereby decreasing the effectiveness of the protection offered by the pad. Some prior art pads include air bladders which provide an air cushion intended to conform to the back. All of these prior art devices achieve only an approximation of a truly proper and anatomically correct fit.

The present invention permits quick and easy application of a lumbosacral support pad to the lower back in such a way as to achieve a true custom fit. The moisture curable resin system used results in a very rigid support pad, which holds the shape of the molded pad to a very high degree. No heat is required, and a source of water is the only additional substance necessary to permanently harden the pad. Atmospheric moisture alone will cure the pad into its hardened position in a relatively short period of time, but the resin in or on the pad will typically be activated by dipping in or spraying water onto the support pad.

SUMMARY OF THE INVENTION

Therefore, it is an object of the invention to provide a lumbosacral support pad which can be custom-molded to the lumbosacral region of the back.

It is another object of the invention to provide a lumbosacral support pad which is usable for treating injuries and for preventing injuries.

It is another object of the invention to provide a lumbosacral support pad which hardens in the presence of moisture to form a very rigid but very lightweight device.

It is another object of the invention to provide a lumbosacral support pad which is stored in a moisture-proof pouch until ready for application to the back.

It is another object of the invention to provide a lumbosacral support pad intended to be inserted into an elastic lumbosacral support member, such as a belt, which encircles the lower torso.

It is another object of the invention to provide a lumbosacral support pad which will not soften or change shape which subjected to body heat.

These and other objects of the present invention are achieved in the preferred embodiments disclosed below by providing a lumbosacral support pad for being custom-fitted to the lumbosacral area of the back and comprising an initially flexible fabric layer comprised of a fabric impregnated or coated with a moisture-curable resin which hardens upon curing to form a rigid structure which retains the shape into which it is molded during curing, a protective covering layer enclosing at least one major surface of the fabric layer, a moisture-proof protective pouch within which the lumbosacral support pad is sealed for storage in the absence of moisture until the pad is to be molded to the back.

According to one preferred embodiment of the invention, the lumbosacral support pad includes a flexible cushion layer positioned on an inner side of the fabric layer for being placed closest to the back.

According to another preferred embodiment of the invention, the fabric layer comprises a plurality of overlaid thicknesses of fiberglass.

According to yet another preferred embodiment of the invention, the plurality of thicknesses of fiberglass comprises at least five thicknesses and no more than seven thicknesses.

According to yet another preferred embodiment of the invention, the cushion layer comprises a foam material.

Preferably, the foam material comprises an EVA closed cell foam.

According to yet another preferred embodiment of the invention, the outer moisture-proof protective pouch is formed of a laminated structure having at least one layer of plastic film and at least one layer of aluminum foil bonded to the plastic film.

According to yet another preferred embodiment of the invention, the initially flexible fabric layer is covered on one major side by an exterior sheeting material and one another major side by a foam material.

According to yet another preferred embodiment of the invention, the pad exterior sheeting material and the foam material are joined together by sewing stitches around the periphery of the lumbosacral support pad.

According to yet another preferred embodiment of the invention, the lumbosacral support pad is supplied in combination with a pouch therein for receiving the lumbosacral support pad and supporting the support pad against the back.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
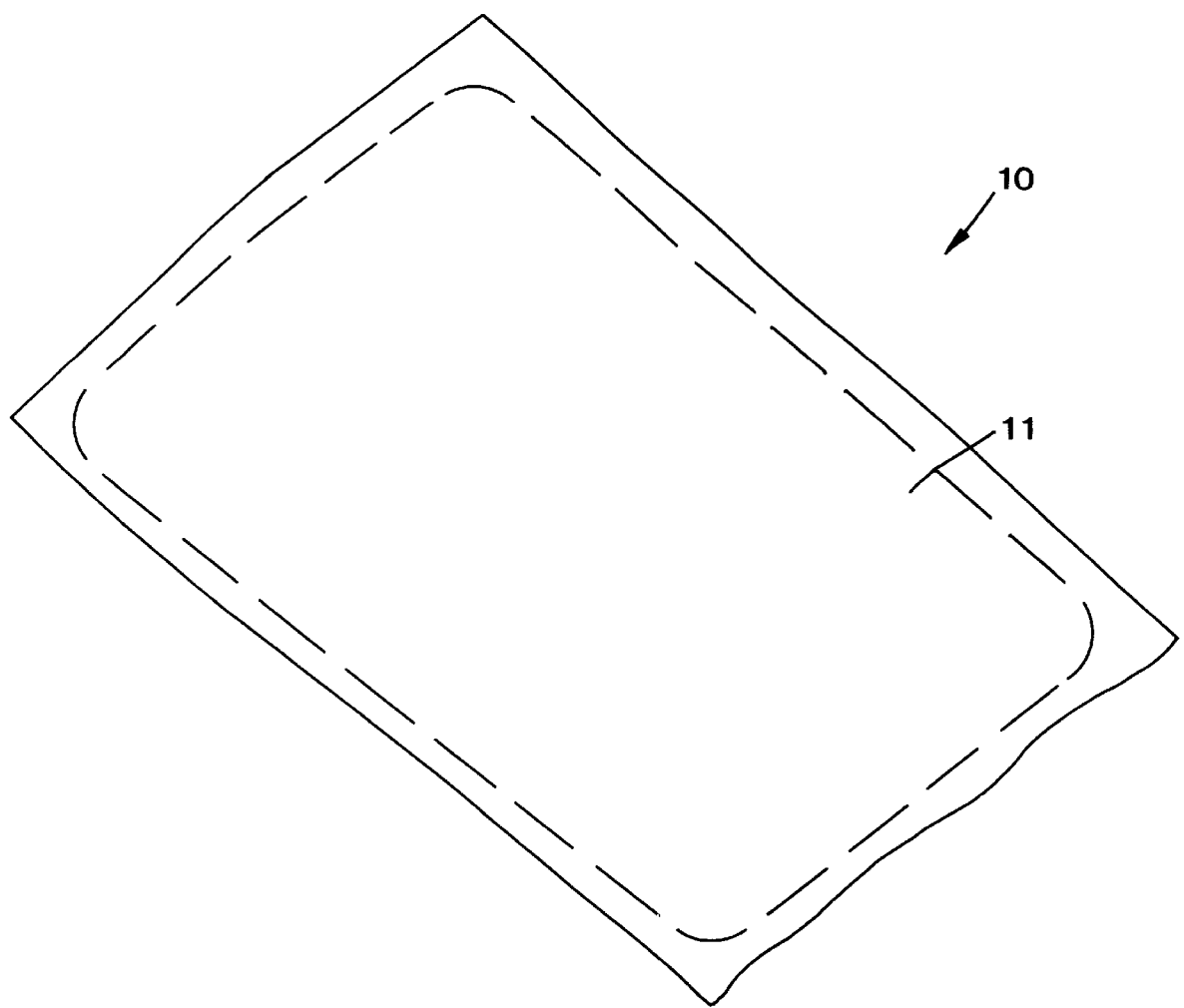
FIG. 1 is a perspective view of a moisture-curable pouch containing a lumbosacral support pad according to an embodiment of the invention.

Referring now specifically to the drawings, FIG. 1 illustrates a lumbosacral support pad assembly 10 according to an embodiment of the invention. The lumbosacral support pad assembly 10 assembly includes as its outermost protective enclosure an outer moisture-impervious laminated foil pouch 11 in which the other components are sealed in the absence of moisture. The preferred structure of the outer moisture-impervious pouch 11 includes a 0.5 mil aluminum foil sheet sandwiched between two layers of low density polyethylene film, each layer having a thickness of 2 mils. Additionally, the pouch 11 can include an outer layer of laminated 60 gauge bi-axially oriented nylon film. This laminate structure, when properly formed into an envelope and sealed, will prevent moisture intrusion indefinitely.

Figure 2:
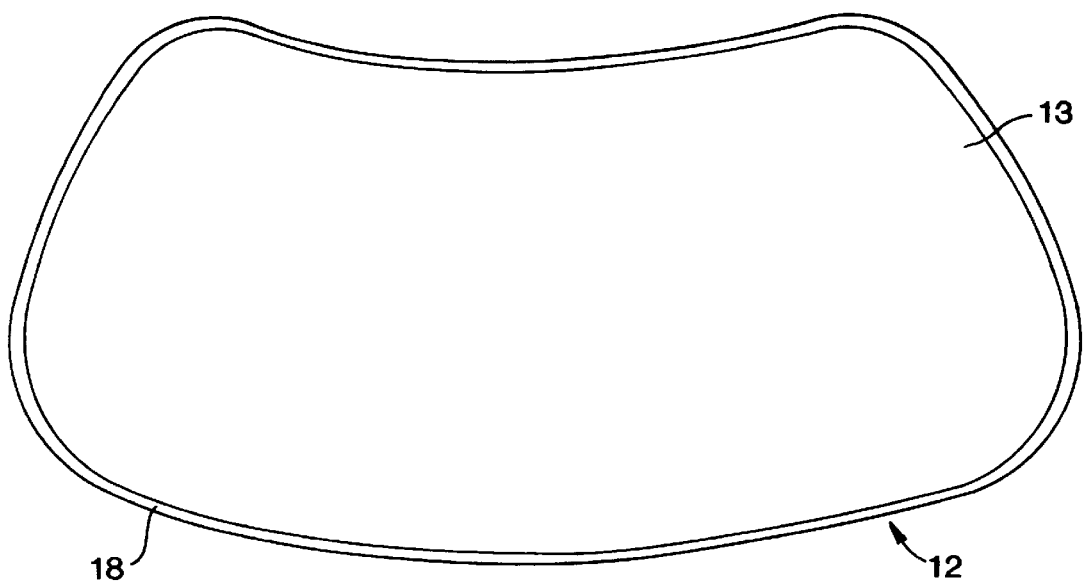
FIG. 2 is a top plan view of the outer side of the lumbosacral support pad according to an embodiment of the invention.
Figure 3:
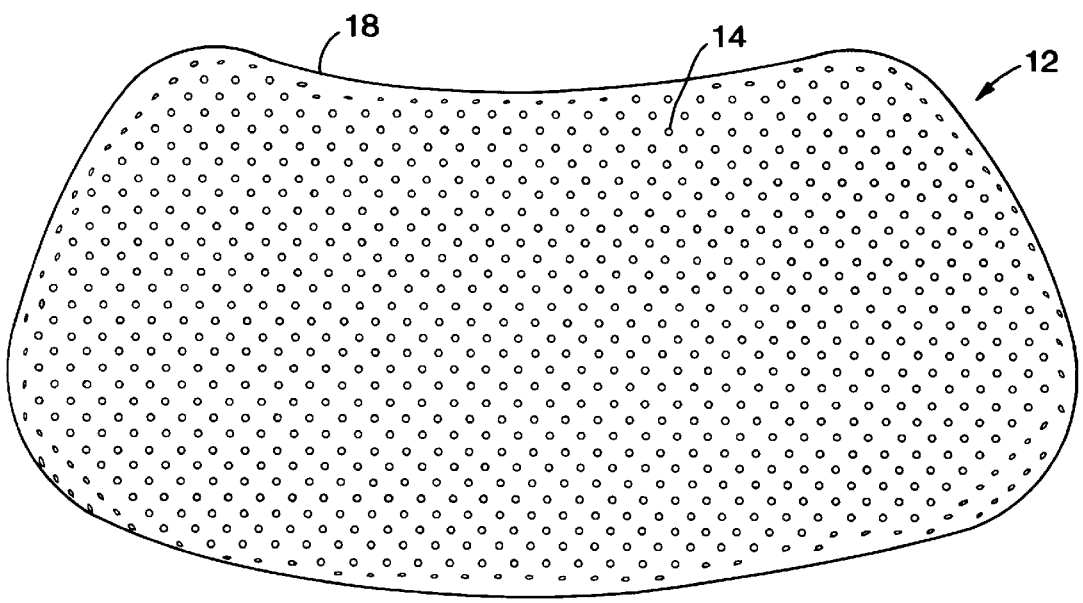
FIG. 3 is a perspective view of the obverse, inner-facing side of the lumbosacral support pad according to the same embodiment of the invention as shown in FIG. 2.

The lumbosacral support pad 12 is illustrated in FIGS. 2 and 3. The outwardly-facing side 13 of the lumbosacral support pad 12 comprises a fabric layer of polyester sheeting, as shown in FIG. 2. The inwardly-facing side of the lumbosacral support pad 12 is shown in FIG. 3, and preferably comprises a ⅛ inch-thick cushion layer 14 of micro-perf four-pound EVA (ethylene vinyl acetate) closed cell foam. The EVA is flexible enough to bend easily with the other components of the lumbosacral support pad 12. Holes are provided in the inwardly-facing foam cushion layer 14 of the lumbosacral support pad 12 to provide ventilation when being worn.

Figure 4:
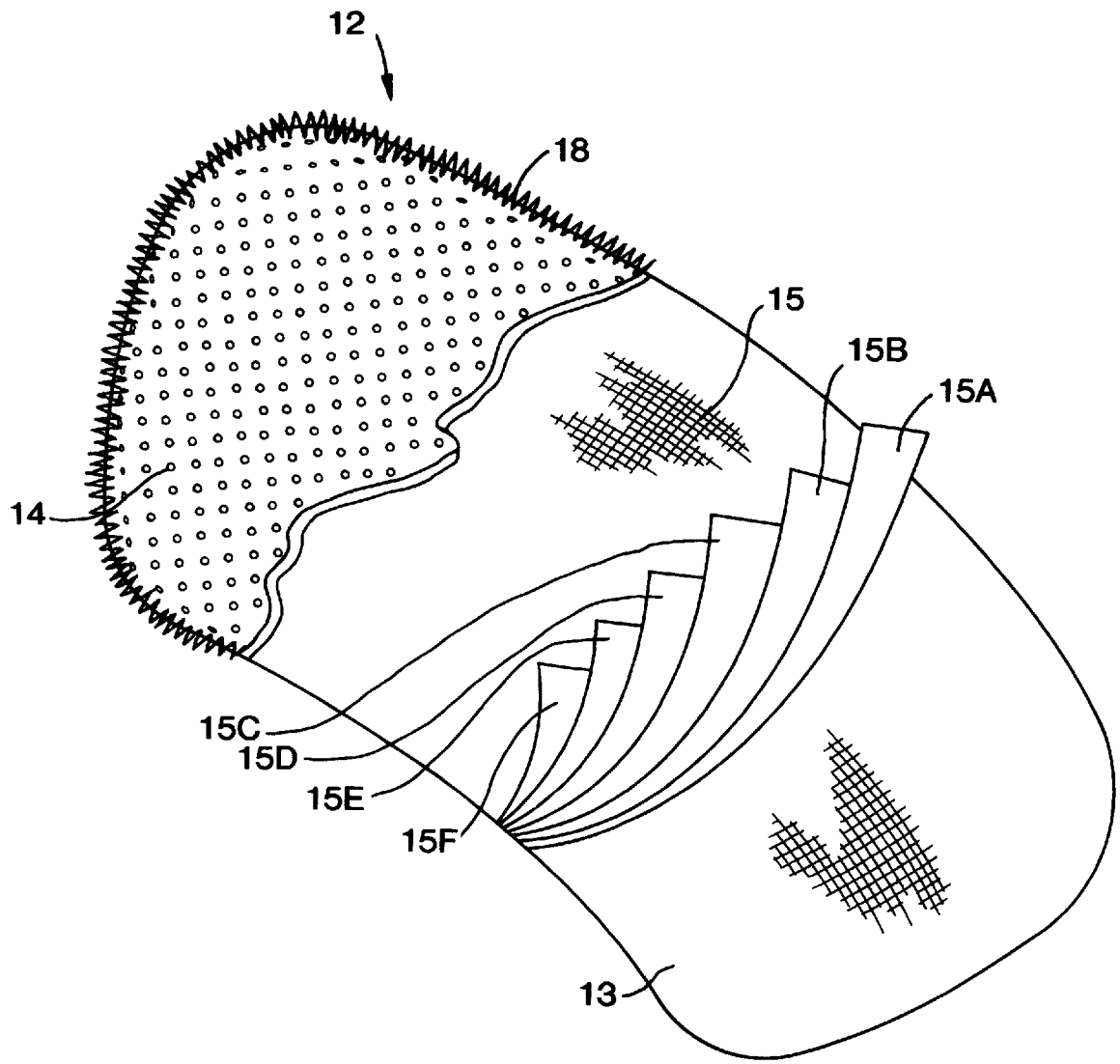
FIG. 4 is a perspective view of a partially-disassembled lumbosacral support pad according to an embodiment of the invention.
Figure 5:
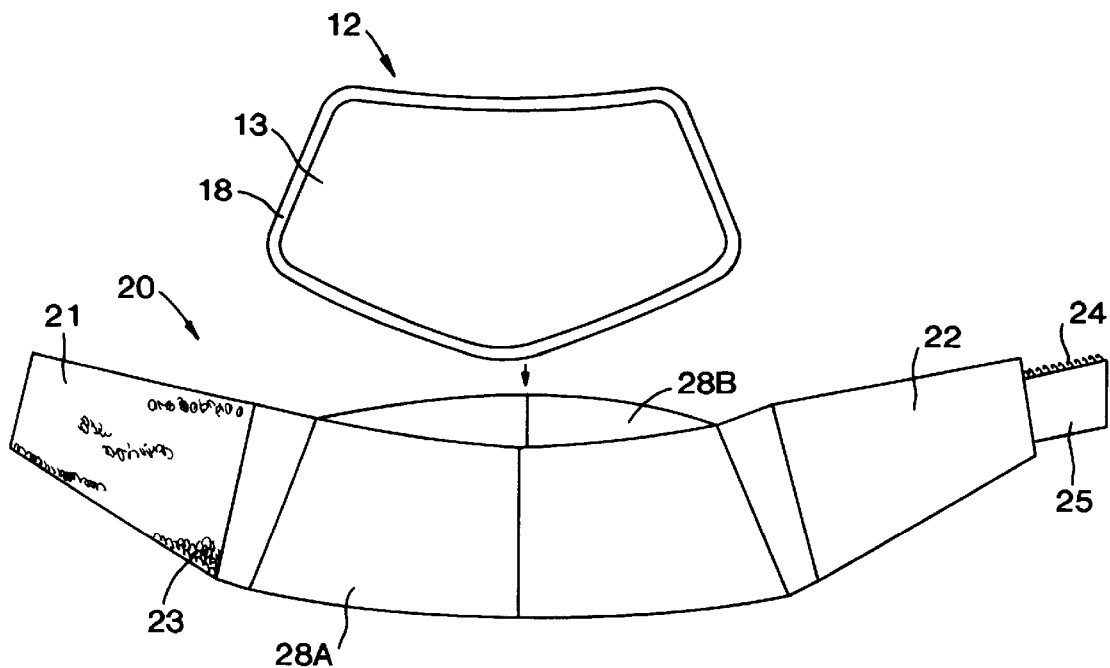
FIG. 5 is a view of the lumbosacral support pad oriented to be inserted into a lumbosacral support belt in accordance with the invention.

As is best shown in FIG. 4, the lumbosacral support pad 12 includes an initially flexible interior fabric layer 15, which is comprised of individual sheets 15A–F of overlaid fiberglass cloth, which may be woven or knitted.

The individual sheets 15A–F of the fabric layer 15 are coated or impregnated with a moisture-curable resin which is flexible in the absence of moisture, but which rapidly hardens when exposed to moisture. One such moisture-curable resin is a polyisocyanate as described in full in the present applicant's U.S. Pat. No. 4,770,299. This reactive system remains stable when maintained in substantially moisture-free conditions, such as in the moisture-impervious pouch 11, but hardens upon exposure to sufficient moisture to form a rigid, self-supporting structure. The number of layers of fiberglass in the protective layer can be varied to take into account anticipated use conditions. Also, as mentioned above, other materials such as a fabric formed of polypropylene can be used in substitution for some of the layers.

A typical formulation of the reaction system is set forth in the following table:

| Typical Formulation: | | |
| --- | --- | --- |
| Isonate↓ 143L | or | |
| Mondur↓ CD | or polyisocyanate | 50.0% |
| Rubinate ↓ XI168 | | |
| Pluracol↓ P1010 | polyol | 46.6% |
| DC-200 Silicone | defoaming agent | 0.30% |
| Benzoyl Chloride | stabilizer | 0.10% |
| Thancat↓ DM-70 | catalyst | 3.0% |
| | 100% | |

A complete discussion of the parameters of the reactive system, the manner of production and the variables which apply are found in U.S. Pat. No. 4,411,262.

The polyisocyanate resin remains in a viscous, liquid unhardened state so long as the resin is not exposed to moisture. This permits the fabric layer 15 and any flexible structure, such as the cushion layer 14 to remain flexible and moldable so long as the resin is not exposed to moisture, and for a relatively short period of time after exposure to moisture. The convex side edges of the pad is that which is defined by the 138 degrees angle shown in FIG. 8. The opposing converging side edges are those located at opposite ends of the convex side edge and extending away therefrom at the 92 degrees angle shown in FIG. 8. The curing time can be controlled to some extent by the quantity of water to which the resin is exposed. For example, exposure to water by dipping will result in quite rapid curing, while merely allowing the resin to be exposed to air will cause long curing times proportional to the amount of humidity in the air to which it is exposed.

Sewing stitches 18, such as over edge seaming stitches, attach the outer fabric layer 13 and the inwardly-facing foam cushion layer 14 at their mutual peripheries with the fiberglass layer 15 trapped by the stitches inside the enclosure thus formed.

The lumbosacral support pad 12 is used in combination with a lumbosacral belt 20. The belt 20 includes two side panels 21 and 22. Side panel 21 has a surface covered with a loose, fibrous, nonwoven material 23, which mates with hooks 24 on one side of an end tab 25 when placed in an encircling position around the lower back of the wearer. Belt 20 also includes center panels 28A, 28B which collectively define between them a pocket into which the lumbosacral support pad 12 is inserted. The center panels 28A, 28B are made of heavy elastic fabric, and the pocket is slightly undersized in relation to the dimensions of the lumbosacral support pad 12, so that when the lumbosacral support pad 12 is inserted into the pocket defined by the panels 28A, 28B, the fabric of the belt 20 stretches and thus tensions the lumbosacral support pad 12 in the pocket. The belt 20 itself is a prior art device sold by Smith & Nephew Rolyan Inc.

Application of the lumbosacral support pad 12 according to the above description is now explained. As noted above, the storage life of the lumbosacral support pad 12 within the heavy foil pouch 11 is indefinite. When ready for application, the foil pouch 11 is cut with a knife or scissors, and the support pad 12 is removed. When removed, the entire structure of the lumbosacral support pad 12 is soft and relatively flexible. Ideally, the lumbosacral support pad 12 is immediately inserted into the pocket of the belt 20, the belt placed around the lower back of the wearer, adjusted for size, and secured in position by engaging the hooks 24 of the end tab 25 with the nonwoven material 23 on the side panel 21.

Figure 6:
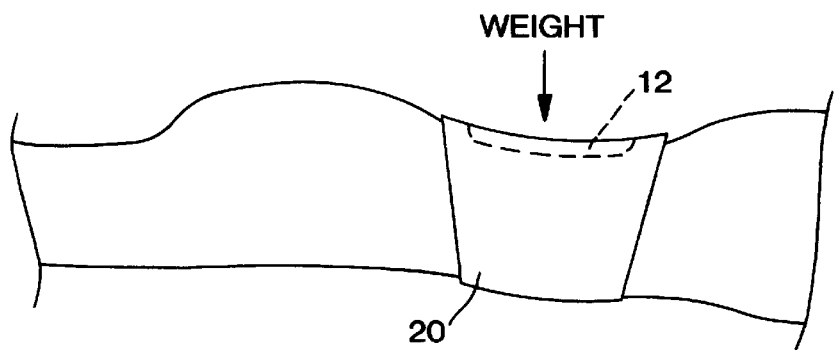
FIG. 6 shows application of the lumbosacral support pad to the lumbosacral region of the back.

The wearer lies face-down as shown in FIG. 6, and sufficient weight is applied to the lumbosacral support pad 12 to form the lumbosacral support pad 12 to the shape of the lumbosacral region of the back without distension. Any suitable weight can be used, but preferably should be a shape-conformable weighted object, such as a bag of small lead weights, which can also conform to the desired shape of the support pad 12. Alternatively, the wearer can lie face-up on a firm, flat surface, and a suitably shape-conformable support such as a towel is placed between the surface and the hollow of the back. In this position the weight of the body urges the support pad 12 down onto the support, thus molding the support pad 12 into the desired shape.

Figure 7:
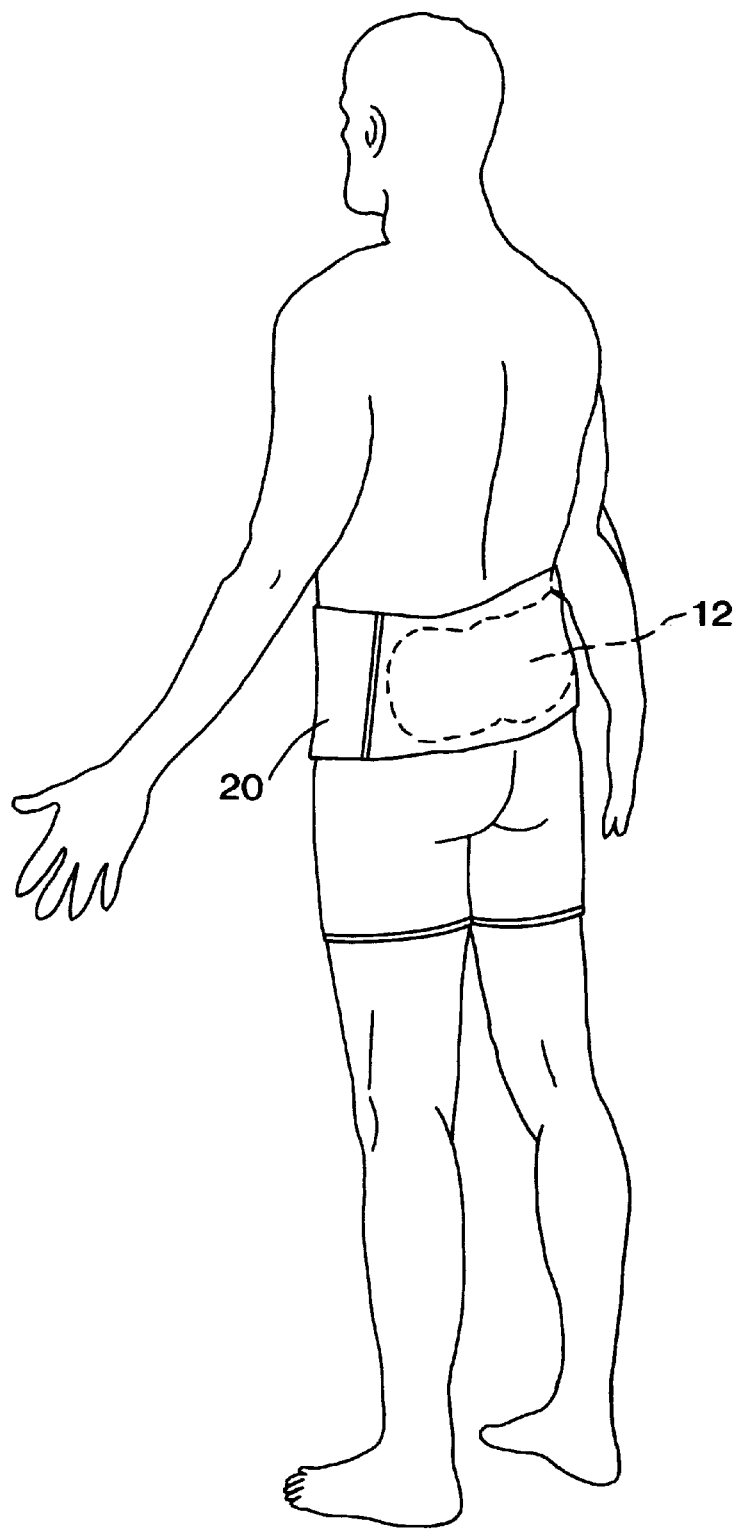
FIG. 7 shows an assembled lumbosacral support pad support belt and support pad in place on the back to which it was molded in FIG. 6.

In no more than approximately 10 minutes, the lumbosacral support pad 12 has hardened fully, and the wearer has a completely custom-fitted lumbosacral support pad 12, as is shown in FIG. 7. The cushion layer 14 retains its soft, pliable feel, but is held in the molded shape by the hardened interior layer 15.

Figure 8:
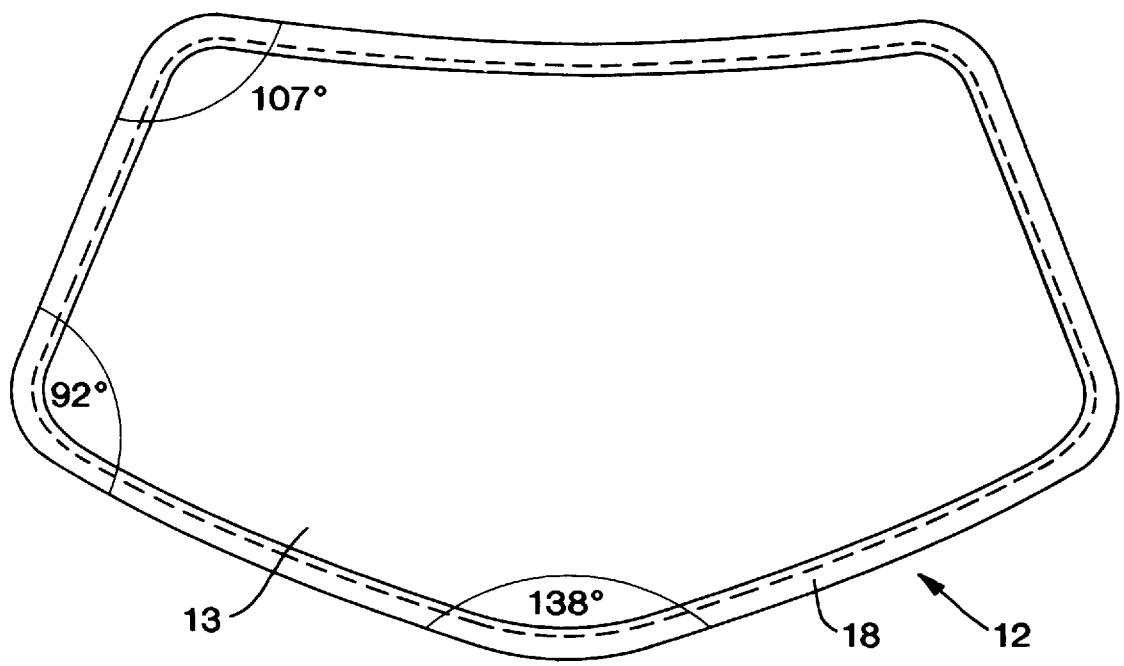
FIG. 8 is a plan view of a preferred lumbosacral support pad having a preferred shape, with indications of preferred dimensions and angles between adjacent sides of the lumbosacral support pad.

The lumbosacral support pad 12 can be made in different sizes and shapes. A preferred size for a lumbosacral support pad 12 for an average-sized adult is approximately 7.5 inches in width and approximately 13.5 to 14 inches in length. A preferred shape is shown in FIG. 8, indicating the angles between adjacent side edges which provide the shape when the noted dimensions are used.

A custom-fitting lumbosacral support pad is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A lumbosacral support pad for being custom-fitted to the lumbosacral area of the back and comprising:
   (a) an initially flexible fabric layer comprised of a plurality of overlaid thicknesses of fiberglass impregnated or coated with a moisture-curable resin which hardens upon curing to form a rigid structure which retains the shape into which it is molded during curing;
   (b) a flexible cushion layer positioned on an inner side of said fabric layer for being placed closest to the back;
   (c) a protective covering layer enclosing at least one major surface of the fabric layer, the fabric layer, said protective covering layer, and said flexible cushion layer being formed in an anatomically-correct shape for being applied and custom-molded to the lumbosacral region of the back; and
   (d) said anatomically-correct shape being defined by two opposing and converging side edges of the pad and at least one convex side edge of the pad, wherein said convex side edge of the pad is adapted to be oriented generally laterally from one side of the back to the other below said converging side edges, said support pad being contained until use within a disposable moisture-proof protective pouch within which the support pad is sealed for storage in the absence of moisture until the support pad is removed from said pouch for being moistened and molded to the back, whereupon the pouch is disposed of.

2. A lumbosacral support pad according to claim 1, wherein said plurality of thicknesses of fiberglass comprises at least five thicknesses and no more than seven thicknesses.

3. A lumbosacral support pad according to claim 1, wherein said cushion layer comprises a foam material.

4. A lumbosacral support pad according to claim 3, wherein said foam material comprises an EVA closed cell foam.

5. A lumbosacral support pad according to claim 1, wherein said initially flexible fabric layer is covered on one major side by an exterior sheeting material and one another major side by a foam material.

6. A lumbosacral support pad according to claim 5, wherein said pad exterior sheeting material and the foam material are joined together by sewing stitches around the periphery of the lumbosacral support pad.

7. A lumbosacral support pad assembly according to claims 2, 3, 4, 5, 6, or 1, and including an elongate elastic belt having a pouch therein for receiving the lumbosacral support pad and supporting the support pad against the back.

* * * * *

UNITED STATES PATENT AND TRADEMARK OFFICE
CERTIFICATE OF CORRECTION

PATENT NO.     : 6,319,217 B1
DATED          : November 20, 2001
INVENTOR(S)    : Darcey, Thomas D.

It is certified that error appears in the above-identified patent and that said Letters Patent is hereby corrected as shown below:

Column 6,
Line 44, delete "one" and insert -- on --.

Signed and Sealed this

Twenty-first Day of January, 2003

JAMES E. ROGAN
*Director of the United States Patent and Trademark Office*